United States Patent [19]

Junge et al.

[11] Patent Number: 5,391,319
[45] Date of Patent: Feb. 21, 1995

[54] LIQUID-CRYSTALLINE MIXTURE

[75] Inventors: Michael Junge, Pfungstadt; Herbert Plach; Alasdair Jelfs, both of Darmstadt; Michael Kompter, Riedstadt, all of Germany

[73] Assignee: Merck Patent Gesellschaft mit Beschrankter Haftung, Darmstadt, Germany

[21] Appl. No.: 153,143

[22] Filed: Nov. 17, 1993

[30] Foreign Application Priority Data

Nov. 18, 1992 [GB] United Kingdom ............... 9224132

[51] Int. Cl.⁶ ................ C09K 19/52; C09K 19/30; C09K 19/20; G02F 1/13
[52] U.S. Cl. ................ 252/299.01; 252/299.63; 252/299.66; 252/299.67; 359/103; 359/106
[58] Field of Search ............ 252/299.01, 299.61, 252/299.65, 299.64, 299.66, 299.67; 359/103, 105

[56] References Cited

U.S. PATENT DOCUMENTS

| | | | |
|---|---|---|---|
| 3,947,375 | 3/1976 | Gray et al. | 252/299.01 |
| 4,001,137 | 1/1977 | Steinstrasser | 252/299.01 |
| 4,130,502 | 12/1978 | Eidenschink et al. | 252/299.01 |
| 4,154,697 | 5/1979 | Eidenschink et al. | 252/299.01 |
| 4,330,426 | 5/1982 | Eidenschink et al. | |
| 4,398,803 | 8/1983 | Pohl et al. | 252/299.01 |
| 5,035,489 | 7/1991 | Iijima et al. | 359/103 |

FOREIGN PATENT DOCUMENTS

| | | |
|---|---|---|
| 2-145684 | 6/1990 | Japan. |
| 2252977 | 8/1992 | United Kingdom. |
| 2258466 | 2/1993 | United Kingdom. |

*Primary Examiner*—Shean Wu
*Attorney, Agent, or Firm*—Millen, White, Zelano & Branigan

[57] ABSTRACT

A liquid-crystalline mixture comprising two or more compounds of the general formula I,

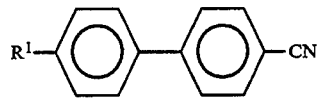

in which $R^1$ is straight-chain alkyl having 3, 5 or 7 carbon atoms, three or more compounds of the general formula II,

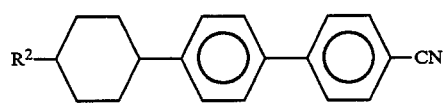

in which $R^2$ is straight-chain alkyl having 2 to 7 carbon atoms, three or more compounds of the general formula III,

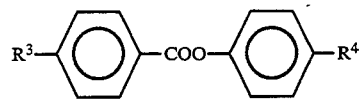

in which $R^3$ and $R^4$ are each independently alkyl or alkoxy with 1 to 10 carbon atoms, and two or more compounds of the general formula IV,

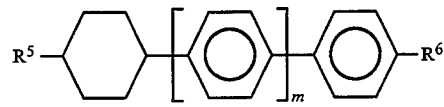

in which $R^5$ and $R^6$ are each independently have one of the meanings indicated for $R^3$ and m is 0 or 1. A "multibottle-system" comprising said mixture and an electro-optical display device based on the principle of the twisted nematic cell.

16 Claims, No Drawings

LIQUID-CRYSTALLINE MIXTURE

FIELD OF THE INVENTION

The present invention relates to a liquid-crystalline mixture of relatively high birefringence, and to the use thereof for electrooptical display devices based on the principle of the twisted nematic cell.

BACKGROUND OF THE INVENTION

Liquid crystals are used, in particular, as dielectrics in display devices since the optical properties of the liquid crystals can be affected by an applied voltage. Electrooptical devices based on liquid crystals are extremely well known to those skilled in the art and may be based on various effects. Devices of this type are, for example, cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The most common display devices are based on the Schadt-Helfrich effect and have a twisted nematic structure.

The liquid-crystal materials must have good chemical and thermal stability and good stability toward electrical fields and electromagnetic radiation, especially in the visible and ultraviolet spectral range. Furthermore, the liquid-crystal materials should have low viscosity and give short addressing times, low threshold voltages, high contrast in the cells and at the same time a wide viewing angle. This wide viewing angle results from the so-called first "minimum" condition (U.S. Pat. No. 4,398,803). The optical path difference, i.e., the product of cell thickness and birefringence, is to be adjusted to about 0.4–0.5 μm. Therefore, for a cell thickness of about 2.5–4 μm, liquid-crystalline mixtures with birefringence of about 0.12 to 0.19 are required. Furthermore, they should have a suitable mesophase, for example, for the above mentioned cells, a nematic or cholesteric mesophase, at customary operating temperatures, i.e., generally in the broadest possible range above and below room temperature. Since liquid crystals are generally used as mixtures of a plurality of components, it is important that the components are readily miscible with one another. Further properties, such as electrical conductivity, dielectric anisotropy and optical anisotropy, must meet various requirements depending on the cell type and the area of application. For example, materials for cells having a twisted nematic structure should have positive dielectric anisotropy and low electrical conductivity.

For display devices addressed with low multiplex ratios (common use displays), which are the preferred subject-matter of the present invention, nematic mixtures having clearing points above 55° (preferably above 65°), birefringence in the range from 0.165 to 0.130 (preferably 0.185 to 0.120) and threshold voltages in the range from 1.20 to 2.20 Volts (preferably from 1.40 to 1.90) are desired.

A known mixture from the prior art is E80A (BDH, Poole, Great Britain), which contains cyanobiphenyls and has the following ethyl-parameters:
$T_{S,N} = -15°$
$T_{N,I} = 60.0°$
$\Delta n = 0.1460$
$\eta_{20} = 41$ cSt
$V_{10}(TN) = 2.07$ volts For many applications, however, mixtures of this type have undesired low birefringence and/or a nematic phase range which is too small for outdoor applications.

It is an object of the invention to provide liquid crystalline mixtures which overcome the inadequacies of the prior art, such as those discussed above.

Upon further study of the specification and appended claims, further objects and advantages of this invention will become apparent to those skilled in the art.

SUMMARY OF THE INVENTION

Accordingly, the invention is directed to a liquid-crystalline mixture consisting essentially of two or more different compounds of the general formula I,

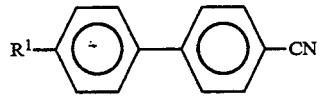

I in which $R^1$ is straight-chain alkyl having 3, 5 or 7 carbon atoms, one or more compounds of the general formula II,

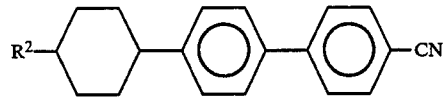

II in which $R^2$ is straight-chain alkyl having 2 to 7 carbon atoms, three or more different compounds of the general formula III,

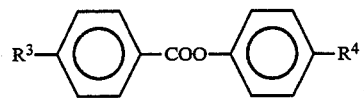

III in which $R^3$ and $R^4$ are each independently alkyl or alkoxy with 1 to 10 carbon atoms, and two or more different compounds of the general formula IV,

IV in which $R^5$ and $R^6$ each independently have one of the meanings indicated for $R^3$ and m is 0 or 1. Preferably, the invention is directed to a liquid-crystalline mixture which contains one or more compounds of the formula IV wherein m is 1 and one or more compounds of the formula IV wherein m is 0. Particularly preferred is a liquid-crystalline mixture wherein the proportion of compounds of the formulae I and II in the total mixture is 15–40% by weight.

DETAILED DESCRIPTION OF THE INVENTION

It has been found that even a relatively small proportion of compounds of the formulae II, III or IV results in a considerable improvement in the addressing times and in the mesophase ranges. The compounds of the formula IV, wherein m is 0, have low optical anisotropy. However, the optical anisotropy of the mixture in the mixing range indicated is decreased only relatively little by the compounds of the formula IV, while the mesophase range is significantly improved. Larger amounts of a compound of the formula I or II generally only cause a slight improvement in the threshold voltage, but a comparatively large increase in the viscosity. The invention thus facilitates liquid-crystal mixtures of low viscosity and short switching times.

The term alkyl with 1 to 10 carbon atoms includes preferably straight-chain alkyl having 2 to 8 carbon atoms including the straight-chain groups ethyl, propyl, butyl, pentyl, hexyl, heptyl, octyl, nonyl and decyl. Groups having 2–7 carbon atoms are generally preferred.

Examples of the preferred alkoxy groups are those having 1–10 carbon atoms, in particular the straight-chain groups methoxy, ethoxy, propoxy, butoxy, pentoxy, hexoxy, heptoxy, octoxy, nonoxy and decoxy. Groups having 1–7 carbon atoms are generally preferred.

The compounds of the formulae I to XI are known or are analogs of known compounds (formula I: GB 14 33 130, corresponding to U.S. Pat. No. 3,947,375; formula II: DE 27 01 591, corresponding to U.S. Pat. No. 4,154,697; formula III: DE 21 67 252, corresponding to U.S. Pat. No. 4,001,137; formula IV (m=0): DE 26 36 684, corresponding to U.S. Pat. No. 4,130,502; (m=1): DE 29 27 277, corresponding to U.S. Pat. No. 4,330,426). Suitable methods for the preparation of these compounds are known to a person skilled in the art.

Formula III includes the non-polar compounds of the general formulae:

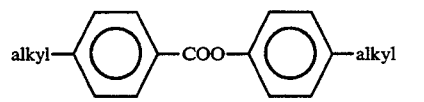
IIIa

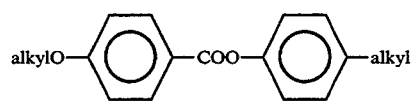
IIIb

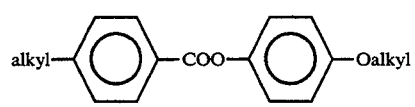
IIIc

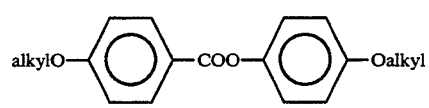
IIId

Formula IV includes the non-polar compounds of the formulae:

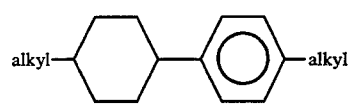
IVa

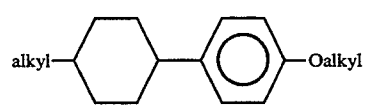
IVb

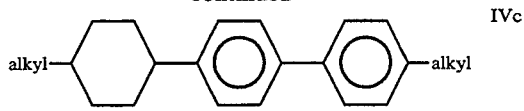
IVc

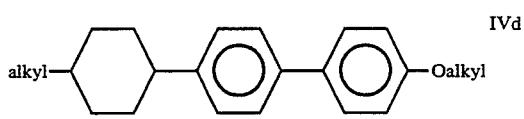
IVd of which IVa and IVb are preferred for achieving particularly low viscosities.

Through a suitable choice of the meanings of $R^1$ to $R^6$ and the meaning of m, the switching times, the threshold voltage, the steepness of the transmission characteristic lines, etc., can be modified in the desired manner.

The optimum mixing ratio of the compounds of the formula I to IV depends substantially on the desired properties, on the choice of the components of the formula I to IV and on the choice of any other components which may be present. Suitable mixing ratios within the above mentioned range can easily be determined from case to case. In general, a ratio between the total weight of compounds of the formula I and the total weight of compounds of the formula II of from about 3:1 to 10:1 is preferred.

The total amount of compounds of the formulae I to IV in the mixtures according to the invention is not crucial. The mixtures can therefore contain one or more further components in order to optimize various properties. However, the observed effect on the addressing times and the threshold voltage is generally greater, the higher the total concentration of the compounds of the formula I to II.

Preferred mixtures according to the invention are therefore those in which the proportion of compounds of the formulae I to II together in the total mixture is at least 10–50% by weight, and in particular those in which the proportion of compounds of the formula I is at least 10% by weight. It goes without saying that the proportion of compounds of the formulae I to IV may also be up to 100% by weight.

Preferred concentration ranges for the compounds of the formulae I to IV arise from the indicated weight ratios and the preferred total amounts. Particular preference is given to mixtures in which the proportion of one or more compounds of the formula II in the total mixture is 3–15% by weight, in particular 3–10% by weight. Furthermore, particularly preferred mixtures are those in which the proportion of one or more compounds of the formula III in the total mixture is at least 35% by weight, in particular at least 40% by weight.

Particular preference is given to mixtures in which the proportion of one or more compounds of the formula IV in the total mixture is 10–30% by weight, in particular 15–25% by weight.

The mixtures according to the invention preferably contain one or more compounds of the formula IV, wherein m is 1 and one or more compounds of the formula IV wherein m is 0.

The total amount of any compounds of the formula IV, wherein m is 1, which may be present in the mixture is preferably at least 5% by weight, particularly preferably at least 10% by weight. If the mixture according to the invention contains one or more compounds of the formula IVb and one or more compounds of the formula IVc the weight ratio between the compounds of the formula IVb and the compounds of the formula IVc is preferably at least 1:10 to 1:1, in particular 1:8 to 1:3.

Liquid-crystal mixtures according the invention consist preferably of:
10–25% by weight of two or more compounds of formula I,
3–15% by weight of one or more compounds of formula II,
40–70% by weight of three or more compounds of formula III and
10–30% by weight of two or more compounds of formula IV.

Particular preference is given to liquid-crystalline mixtures consisting of compounds of formulae I to IV wherein
$R^1$ is n-alkyl with 3 or 5C atoms,
$R^2$ is n-alkyl with 2, 3 or 5C atoms,
$R^3$ is n-alkyl or n-alkoxy with 1 to 8C atoms,
$R^4$ is n-alkyl or n-alkoxy with 5C atoms,
$R^5$ is n-alkyl with 3 or 5C atoms,
$R^6$ is n-alkyl or n-alkoxy with 1 to 4C atoms.

Further preference is given to liquid crystalline mixtures containing:
2 compounds of formula I,
1 compound of formula II,
5 compounds of formula III and
3 compounds of formula IV,
in particular containing 2 compounds of formulae III wherein $R^3$ is alkoxy and 3 compounds of formula III wherein $R^3$ is alkyl, and, further, in particular, containing 2 compounds of formula IV, wherein m is 1, and 1 compound of formula IV, wherein m is 0.

The mixtures according to the invention are particularly suitable for nematic and cholesteric applications. The mixture of the compounds of the formulae I, II, III and/or IV can be used as such or mixed with further liquid-crystalline and/or non-liquid-crystalline components. Suitable further components are known to a person skilled in the art and some are commercially available, such as, for example, nematic or nematogenic (monotropic or isotropic) substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-biscyclohexylbiphenyls, phenyl- or cyclohexylpyrimidines, phenyl- or cyclohexylpyridines, phenyl- or cyclohexyldioxanes, phenylor cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)-ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

Preferred compounds suitable as further, optional, constituents of media according to the invention can be characterized by the formulae 1, 2, 3, 4 and 5:

$$R'-L-E-R'' \quad (1)$$

$$R'-L-COO-E-R'' \quad (2)$$

$$R'-L-OOC-E-R'' \quad (3)$$

$$R'-L-CH_2CH_2-E-R'' \quad (4)$$

$$R'-L-C\equiv C-E-R' \quad (5)$$

In the formulae 1, 2, 3, 4 and 5, L and E, which may be identical or different, are in each case, independently of one another, a bivalent radical from the group of -Phe-, -Cyc-, -Phe-Phe-, -Phe-Cyc-, -Cyc-Cyc-, -Pyr-, -Dio-, -G-Phe- and their mirror images, where Phe is unsubstituted or fluorine-substituted 1,4-phenylene, Cyc is trans-1,4-cyclohexylene or 1-4-cyclohexenylene, Pyr is pyrimidine-2,5-diyl or pyridine-2,5-diyl, Dio is 1,3-dioxane-2,B-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group comprising -Phe-Cyc-, -Cyc-Cyc-, -G-Phe- and -G-Cyc-.

In a preferred sub-group of the compounds of the formulae 1, 2, 3, 4 and 5, R' and R' are in each case, independently of one another, alkyl, alkenyl, alkoxy, alkenyloxy or alkanoyloxy having up to 8 carbon atoms (group 1). In most of these compounds, R' and R' are different from one another, one of these radicals usually being alkyl or alkenyl. In a further preferred sub-group of the compounds of the formulae 1, 2, 3, 4 and 5, R' is —CN, —CF$_3$, F, Cl, —OCN or —NCS; in this case, R has the meaning given for the compounds of group 1 and is preferably alkyl or alkenyl (group 2). However, other variants of the proposed substituents in the compounds of the formulae 1, 2, 3, 4 and 5 are common. Many such substances or alternatively mixtures thereof are commercially available. All these substances can be obtained by methods which are known from the literature or in a manner analogous thereto.

Besides components from group 1, the mixtures according to the invention preferably also contain components from group 2, whose proportions are preferably as follows:
group 1: 20 to 90%, in particular 30 to 90%
group 2: 10 to 80%, in particular 10 to 50%
the sum of the proportions of the compounds of the formulae I, II, III and IV and of the compounds from groups 1 and 2 adding up to 100%.

The mixtures according to the invention preferably contain 1 to 40%, in particular preferably 5 to 30%, of compounds of formulae I, II, III and IV. Further preferred media are those which contain more than 40%, in particular 45 to 90%, of compounds according to the formulae I to IV. The media preferably contain eight, nine or ten compounds according to the formulae I to IV.

Besides the compounds of the formulae I, II, III and/or IV the liquid-crystalline mixtures according to the invention preferably contain, as the further constituents, 2 to 40, in particular 4 to 30, components. These mixtures very particularly preferably contain 7 to 25 components in addition to the compounds of the formulae I, II, III and/or IV.

In order to match the material parameters to the respective display parameters, the media according to the invention are prepared, in a particularly preferred embodiment, by mixing so-called "multibottle systems". A "two-bottle or multibottle system" usually allows the required optical anisotropy to be adjusted in accordance with the layer thickness of the TN displays.

In addition, the "multibottle system" according to the invention allows the threshold voltage to be adjusted at a pre-specified optical anisotropy.

A multibottle system useful for the invention comprises two or more liquid crystalline components of which at least two components have nearly identical threshold voltages but different optical anisotropies or at least two components have nearly identical optical anisotropies, but different threshold voltages, wherein one component, (A), is a liquid crystalline medium according to the invention described herein. Preferably, component (A) consists of compounds of the formulae I to IV, defined above.

Preferred multibottle systems are:

a) A multibottle system wherein component (A) has an optical anisotropy of 0.150–0.165, and another component (B) has an optical anisotropy of 0.110–0.125 and nearly identical threshold voltage to (A), in particular wherein component (B) consists essentially of compounds selected from the formulae III, IV wherein m is 0, and V to VII:

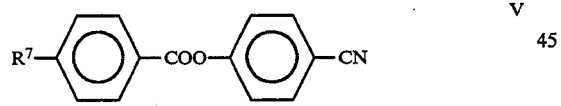

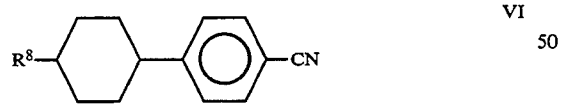

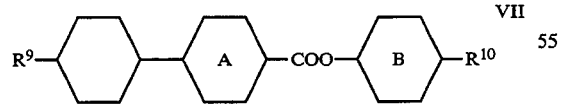

where $R^7$, $R^8$, $R^9$ and $R^{10}$ have the meanings indicated for $R^3$ and $R^4$ above, and

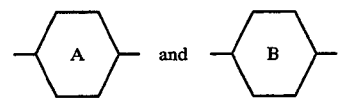

are each independently

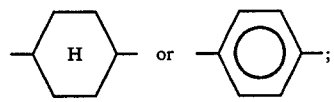

b) A multibottle system wherein component (A) has a threshold voltage of about 2 Volts and another component (C) has a threshold voltage of about 1.25 Volts and nearly identical optical anisotropy to (A), in particular wherein component (C) consists essentially of compounds selected from the formulae I, III, IV, V, VIII and IX

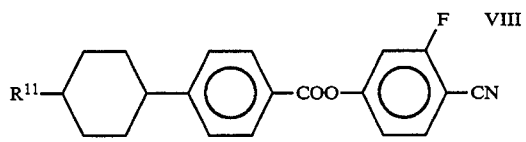

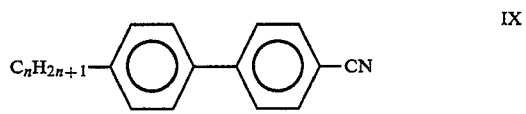

wherein $R^{11}$ has one of the meaning indicated for $R^3$, and n is 2, 4 or 6;

c) a multibottle system as described above for a) and b) having a further component (D) with an optical anisotropy of 0.110–0.125 and a threshold voltage of about 1.25 Volts, in particular wherein component (D) consists essentially of compounds selected from formulae III, IV, wherein m is 0, VI, VIII, X and XI:

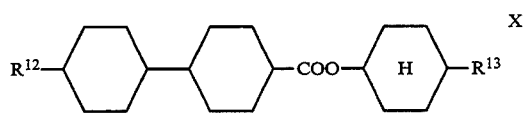

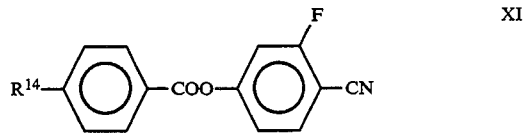

wherein $R^{12}$, $R^{13}$ and $R^{14}$ have one of the meanings indicated for $R^3$.

The invention furthermore relates to an electrooptical display device based on the principle of the twisted nematic cell, characterized in that it contains a liquid crystalline medium as described herein or a liquid crystalline medium obtainable from the multibottle systems described herein as dielectric.

The mixtures according to the invention may also contain one or more optically active compounds. Examples of suitable optically active compounds are the cholesteryl derivatives (for example cholesteryl chloride or cholesteryl nonanoate), and the optically active compounds of the formulae I-V with a chiral side chain [for example optically active 4-(2-methyl- butyl or 2-methylbutoxy)-4-biphenylcarbonitrile]. The mixtures according to the invention may furthermore contain one or more dichroic dyes (for example azo, azoxy and/or anthraquinone dyes). The proportion of optically active compounds and/or dyes is determined by the solubility, the desired pitch, color, extinction and the like. In general, the proportion of optically active compounds with dichroic dyes is at most in each case about 10% by weight, preferably 0.5 to 8.0% by weight, in the total mixture.

The mixtures according to the invention and the electrooptical devices which contain this mixture as liquid-crystalline dielectric can be produced by methods known per se.

The invention is illustrated further by the examples below. C denotes a crystalline phase, S a smectic phase, $S_B$ a smectic B phase, N a nematic phase and I the isotropic phase. $V_{10}$ denotes the voltage for 10% transmission (view angle perpendicular to the plate surface). $t_{on}$ denotes the switch-on time and $t_{off}$ the switch-off time at an operating voltage corresponding to 2.5 times the value of $V_{10}$. $\Delta n$ denotes the optical anisotropy. The electrooptical data were measured at 20° C. in a TN cell at a plate separation matched to the optical delay desired, unless expressly stated otherwise. The optical data were measured at 20° C., unless expressly stated otherwise.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding British application GB 9224132.2, filed Nov. 18, 1992, are hereby incorporated by reference.

EXAMPLES

The structures of the liquid crystalline compounds in the following examples are given by acronyms. The transformation into chemical formulae is explained by the following abbreviations:

| Code for $R^1$, $R^2$ and $L^1$ | $R^1$ | $R^2$ | $L^1$ |
|---|---|---|---|
| nm | $C_nH_{2n+1}$ | $C_mH_{2m+1}$ | H |
| nOm | $C_nH_{2n+1}$ | $OC_mH_{2m+1}$ | H |
| n | $C_nH_{2n+1}$ | CN | H |
| nN.F | $C_nH_{2n+1}$ | CN | F |
| nO.m | $C_nH_{2n+1}O$ | $C_mH_{2m+1}$ | H |
| nN | $C_nH_{2n+1}$ | CN | H |

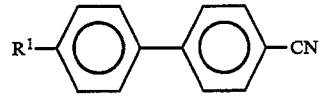

K3n

BCH-n

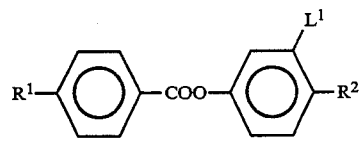

ME

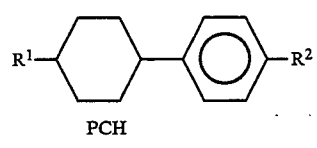

PCH

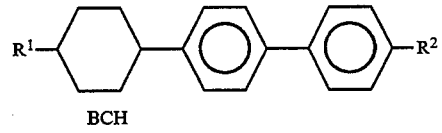

BCH

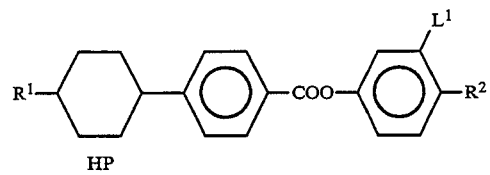

HP

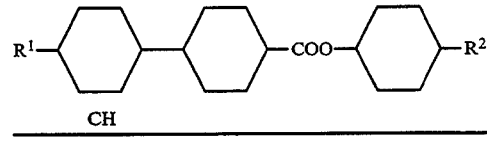

CH

EXAMPLE 1

A mixture comprising

| K9 | 9.0% |
| K15 | 9.0% |
| BCH-5 | 5.0% |
| ME60.5 | 16.0% |
| ME10.5 | 22.0% |
| ME15 | 7.0% |
| ME35 | 7.0% |
| ME55 | 6.0% |
| BCH-32 | 10.0% |
| BCH-52 | 6.0% |
| PCH-301 | 3.0% | exhibits the following properties:
$T_{S,N} < -20°$ C.
$T_{N,I} + 65°$ C.
Viscosity (20° C.): 44 mm²/s
$\Delta n$ (20° C.): 0.1601
$V_{(10,0,20)}$: 2.09 Volts

EXAMPLE 2

A "4-bottle-system" is produced comprising components A, B, C and D:

Component A is identical with the mixture disclosed by example 1.

| B | | C | | D | |
|---|---|---|---|---|---|
| ME2N | 2.0% | PCH-3 | 18.0% | PCH-3 | 20.0% |
| ME3N | 2.0% | PCH-301 | 7.0% | PCH-5 | 11.0% |
| PCH-2 | 4.0% | K12 | 13.0% | PCH-301 | 18.0% |
| PCH-3 | 4.0% | K15 | 13.0% | ME3N.F | 3.0% |
| PCH-4 | 4.0% | ME2N | 6.0% | ME5N.F | 8.0% |
| PCH-5 | 4.0% | ME3N | 6.0% | ME60.5 | 16.0% |
| HP-33 | 5.0% | ME60.5 | 17.0% | CH-33 | 5.0% |
| HP-35 | 3.0% | HP-3N.F | 5.0% | CH-43 | 5.0% |
| HP-53 | 4.0% | HP-5N.F | 5.0% | HP-3N.F | 5.0% |
| CH-35 | 4.0% | BCH-52 | 10.0% | HP-4N.F | 4.0% |
| CH-43 | 4.0% | | | HP-5N.F | 5.0% |
| CH-45 | 4.0% | | | | |
| ME10.5 | 21.0% | | | | |
| ME60.5 | 21.0% | | | | |
| PCH-301 | 14.0% | | | | |

Component B has the following parameters:
S < −30N+66I
Viscosity (20° C.): 37 mm²/s
Δn(20°'C.): 0.1164
$V_{(10,0,20)}$: 2.09V Component C has the following parameters:
S < −40N+61I
Viscosity (20° C.): 40 mm²/s
Δn (20°'C.): 0.1601
$V_{(10,0,20)}$: 1.25V Component D has the following parameters:
S < −40N+63I
Viscosity (20° C.): 35 mm²/s
Δn (20°'C.): 0.1204
$V_{(10,0,20)}$: 1.23V Mixing components A and B gives mixtures having the following parameters:

| Component (%) | | | $V_{(10,0,20)}$ |
|---|---|---|---|
| A | B | Δn | (Volts) |
| 25 | 75 | 0.127 | 2.09 |
| 50 | 50 | 0.138 | 2.09 |
| 75 | 25 | 0.149 | 2.09 |

Mixing components A and C gives mixtures having the following parameters:

| Component (%) | | | $V_{(10,0,20)}$ |
|---|---|---|---|
| A | C | Δn | (Volts) |
| 25 | 75 | 0.1601 | 1.46 |
| 50 | 50 | 0.1601 | 1.66 |
| 75 | 25 | 0.1601 | 1.88 |

Mixing components A and D gives mixtures having the following parameters:

| Component (%) | | | V(10,0,20) |
|---|---|---|---|
| A | D | Δn | (Volts) |
| 25 | 75 | 0.128 | 1.45 |
| 50 | 50 | 0.139 | 1.65 |
| 75 | 25 | 0.150 | 1.87 |

The novel "4-bottle-system" allows for adjustment of the parameters Δn and $V_{(10,0,20)}$ between 0.1164 to 0.1601 and between 1.23 Volts to 2.09 Volts by admixing the 4 base mixtures in the corresponding amounts.

We claim:

1. A liquid-crystalline mixture comprising two or more compounds of the formula I,

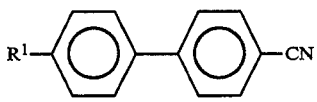

in which $R^1$ is a straight-chain alkyl having 3, 5 or 7 carbon atoms, one or more compounds of the formula II,

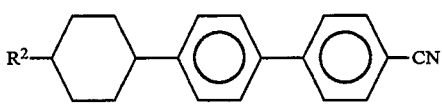

in which $R^2$ is a straight-chain alkyl having 2 to 7 carbon atoms, three or more compounds of the formula III,

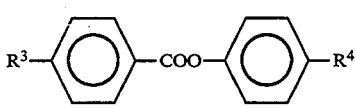

in which $R^3$ and $R^4$ are each independently alkyl or alkoxy with 1 to 10 carbon atoms, and two or more compounds of the formula IV,

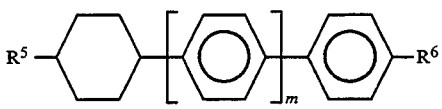

in which $R^5$ and $R^6$ each independently have one of the meanings indicated for $R^3$ and m is 0 or 1.

2. The liquid-crystalline mixture of claim 1, which comprises one or more compounds of the formula IV wherein m is 1 and one or more compounds of the formula IV wherein m is 0.

3. The liquid-crystalline mixture of claim 1, wherein the proportion of compounds of the formulae I and II in the total mixture is 15–40% by weight.

4. The liquid-crystalline mixture of claim 1, wherein the proportion of compounds of the formula I in the total mixture is at least 10% by weight.

5. The liquid-crystalline mixture of claim 1, consisting essentially of
10–25% by weight of two or more compounds of formula I,
3–15% by weight of one or more compounds of formula II,
40–70% by weight of three or more compounds of formula III, and
10–30% by weight of two or more compounds of formula IV.

6. The liquid-crystalline mixture of claim 1, wherein
$R^1$ is n-alkyl with 3 or 5C atoms,
$R^2$ is n-alkyl with 2, 3 or 5C atoms,
$R^3$ is n-alkyl or n-alkoxy with 1 to 8C atoms,
$R^4$ is n-alkyl or n-alkoxy with 5C atoms,
$R^5$ is n-alkyl with 3 or 5C atoms, and $R^6$ is n-alkyl or n-alkoxy with 1 to 4C atoms.

7. The liquid-crystalline mixture of claim 1, which contains
2 compounds of formula I,
1 compound of formula II,
5 compounds of formula III, and
3 compounds of formula IV.

8. The liquid-crystalline mixture of claim 1, which contains 2 compounds of formulae III, wherein $R^3$ is alkoxy, and 3 compounds of formula III wherein $R^3$ is alkyl.

9. The liquid-crystalline mixture of claim 1, which contains 2 compounds of formula IV, wherein m is 1, and 1 compound of formula IV, where m is 0.

10. An electrooptical display device based on the principle of the twisted nematic cell, containing a liquid crystalline mixture according to claim 1 as dielectric.

11. A liquid-crystalline mixture consisting essentially of
10-25% by weight of two or more compounds of the formula I,

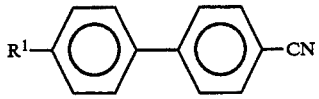
I in which $R^1$ is a straight-chain alkyl having 3, 5 or 7 carbon atoms,
3-15% by weight of one or more compounds of the formula II,

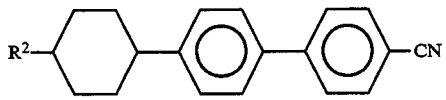
II in which $R^2$ is a straight-chain alkyl having 2 to 7 carbon atoms,
40-70% by weight of three or more compounds of the formula III,

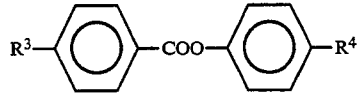
III in which $R^3$ and $R^4$ are each independently alkyl or alkoxy with 1 to 10 carbon atoms, and
10-30% by weight of two or more compounds of the formula IV,

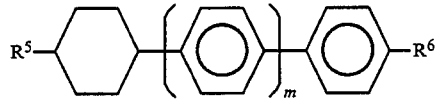

in which $R^5$ and $R^6$ each independently have one of the meanings indicated for $R^3$ and m is 0 or 1.

12. An electrooptical display according to claim 10 based on the principal of the twisted nematic cell, wherein the liquid crystalline mixture has the following properties:
 a. clearing point above 65° C.;
 b. birefringence of 0.130 to 0.165; and
 c. threshold voltage of 1.20 to 2.20 volts.

13. An electrooptical display based on the twisted nematic cell, containing a liquid crystalline mixture according to claim 11 as dielectric.

14. An electrooptical display according to claim 13 based on the principal of the twisted nematic cell, wherein the liquid crystalline mixture has the following properties:
 a. clearing point above 65° C.;
 b. birefringence of 0.130 to 0.165; and
 c. threshold voltage of 1.20 to 2.20 volts.

15. The liquid crystalline mixture of claim 1 having the following properties:
 a. clearing point above 65° C.,
 b. birefringence of 0.130 to 0.165, and
 c. threshold voltage of 1.20 to 2.20 volts.

16. The liquid crystalline mixture of claim 11 having the following properties:
 a. clearing point above 65° C.,
 b. birefringence of 0.130 to 0.165, and
 c. threshold voltage of 1.20 to 2.20 volts.

* * * * *